United States Patent
Martinez Botella et al.

(10) Patent No.: US 11,773,088 B2
(45) Date of Patent: Oct. 3, 2023

(54) KCNT1 INHIBITORS AND METHODS OF USE

(71) Applicant: Praxis Precision Medicines, Inc., Cambridge, MA (US)

(72) Inventors: Gabriel Martinez Botella, Wayland, MA (US); Andrew Mark Griffin, L'Ile Bizard (CA)

(73) Assignee: Praxis Precision Medicines, Inc., Boston, MA (US)

( * ) Notice: Subject to any disclaimer, the term of this patent is extended or adjusted under 35 U.S.C. 154(b) by 0 days.

(21) Appl. No.: 17/517,028

(22) Filed: Nov. 2, 2021

(65) Prior Publication Data
US 2022/0135553 A1    May 5, 2022

Related U.S. Application Data

(60) Provisional application No. 63/108,588, filed on Nov. 2, 2020.

(51) Int. Cl.
*C07D 413/14*     (2006.01)

(52) U.S. Cl.
CPC .................. *C07D 413/14* (2013.01)

(58) Field of Classification Search
CPC .................................................. C07D 413/14
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,902,514 | A | 2/1990 | Barclay et al. |
| 4,992,445 | A | 2/1991 | Lawter et al. |
| 5,001,139 | A | 3/1991 | Lawter et al. |
| 5,023,252 | A | 6/1991 | Hseih |
| 5,616,345 | A | 4/1997 | Geoghegan et al. |
| 6,221,866 | B1 | 4/2001 | Brendel et al. |
| 9,321,727 | B2 | 4/2016 | Bissantz et al. |
| 2003/0055093 | A1 | 3/2003 | Strobel et al. |
| 2004/0266823 | A1 | 12/2004 | Cumming et al. |
| 2008/0021217 | A1 | 1/2008 | Borchardt et al. |
| 2008/0269241 | A1 | 10/2008 | Allen et al. |
| 2015/0105386 | A1 | 4/2015 | Mack et al. |
| 2018/0036295 | A1 | 2/2018 | Cheng et al. |
| 2018/0072708 | A1 | 3/2018 | Yanagisawa et al. |
| 2019/0022039 | A1 | 1/2019 | Fujii et al. |

FOREIGN PATENT DOCUMENTS

| | | |
|---|---|---|
| WO | WO-2020227097 A1 | 11/2020 |
| WO | WO-2020227101 A1 | 11/2020 |
| WO | WO-2021173930 A1 | 9/2021 |
| WO | WO-2021195066 A2 | 9/2021 |
| WO | WO-2022010880 A1 | 1/2022 |

OTHER PUBLICATIONS

Albrecht et al., (2008). "Discovery and optimization of substituted piperidines as potent, selective, CNS-penetrant a4b2 nicotinic acetylcholine receptor potentiators", Bioorganic & Medicinal Chemistry Letters, 18:5209-5212.

Barcia et al., (2012). "De novo gain of function KCNT1 channel mutations cause malignant migrating partial seizures of infancy," Nat Genet., 44(11):1255-1259, 14 pages.

Baumer et al. (2017). "Quinidine-associated skin discoloration in KCNT1-associated pediatric epilepsy," Neurology, 89(21):2212, 3 pages.

Berge et al., (1977). "Pharmaceutical Salts," J. Pharmaceutical Sciences, 66:1-19.

Dilena et al., (2018). "Early Treatment with Quinidine in 2 Patients with Epilepsy of Infancy with Migrating Focal Seizures (EIMFS) Due to Gain-of-Function KCNT1 Mutations: Functional Studies, Clinical Responses, and Critical Issues for Personalized Therapy," Neurotherapeutics, 15(4):1112-1126.

Epi4K Consortium & Epilepsy Phenome/Genome Project, (2013). "De novo mutations in epileptic encephalopathies," Nature, 501:217-221, 16 pages.

Fukuoka et al., (2017). "Quinidine therapy for West syndrome with KCNTI mutation: A case report," Brain Dev., 39:80-83.

Gould, (1986). "Salt selection for basic drugs," International Journal of Pharmaceutics, 33:201-217.

Heron et al., (2012). "Missense mutations in the sodium-gated potassium channel gene KCNT1 cause severe autosomal dominant nocturnal frontal lobe epilepsy," Nat Genet., 44:1188-1190.

International Search Report and Written Opinion for International Patent Application No. PCT/US2020/031039 dated Sep. 11, 2020, 14 pages.

International Search Report and Written Opinion for International Patent Application No. PCT/US2020/031046 dated Sep. 4, 2020, 13 pages.

International Search Report and Written Opinion for International Patent Application No. PCT/US2021/019814 dated Jul. 1, 2021, 12 pages.

International Search Report and Written Opinion for International Patent Application No. PCT/US2021/023653 dated Sep. 14, 2021, 10 pages.

International Search Report and Written Opinion for International Patent Application No. PCT/US2021/040486 dated Oct. 20, 2021, 9 pages.

(Continued)

*Primary Examiner* — Kamal A Saeed
(74) *Attorney, Agent, or Firm* — MH2 Technology Law Group

(57) ABSTRACT

The present invention is directed to, in part, compounds and compositions useful for preventing and/or treating a neurological disease or disorder, a disease or condition relating to excessive neuronal excitability, and/or a gain-of-function mutation in a gene (e.g., KCNT1). Methods of treating a neurological disease or disorder, a disease or condition relating to excessive neuronal excitability, and/or a gain-of-function mutation in a gene such as KCNT1 are also provided herein.

19 Claims, No Drawings

(56) References Cited

OTHER PUBLICATIONS

Ishii et al., (2013). "A recurrent KCNT1 mutation in two sporadic cases with malignant migrating partial seizures in infancy," Gene, 531:467-471.
Kawasaki et al., (2017). "Three Cases of KCNT1 Mutations: Malignant Migrating Partial Seizures in Infancy with Massive Systemic to Pulmonary Collateral Arteries," J Pediatr., 191:270-274.
Kim et al., (2014). "Human slack potassium channel mutations increase positive cooperativity between individual channels," Cell Rep., 9(5):1661-1672.
Lim et al., (2016). "KCNT1 mutations in seizure disorders: the phenotypic spectrum and functional effects," J Med Genet., 53:217-25.
Madaan et al., (2017). "A quinidine non responsive novel KCNT1 mutation in an Indian infant with epilepsy of infancy with migrating focal seizures," Brain Dev., 40(3):229-232.
McTague et al., (2013). "Migrating partial seizures of infancy: expansion of the electroclinical, radiological and pathological disease spectrum," Brain, 136:1578-1591.
McTague et al., (2018). "Clinical and molecular characterization of KCNT1-related severe early-onset epilepsy," Neurology, 90(1):e55-e66.
Mikati et al., (2015). "Quinidine in the treatment of KCNT1-positive epilepsies," Ann Neurol., 78(6):995-999.
Milligan et al., (2015). "KCNT1 gain of function in 2 epilepsy phenotypes is reversed by quinidine," Ann Neurol., 75(4):581-590.
Moller et al., (2015). "Mutations in KCNT1 cause a spectrum of focal epilepsies," Epilepsia, 56:e114-20.
Numis et al., (2018). "Lack of response to quinidine in KCNT1-related neonatal epilepsy," Epilepsia, 59:1889-1898, 10 pages.
Ohba et al., (2015). "De novo KCNT1 mutations in early-onset epileptic encephalopathy," Epilepsia, 56:e121-e128.
Pubchem, (2007). "N-Benzyl-5-sulfamoylthiophene-2-carboxamide: CID 22901904," Available online at <https://pubchem.ncbi.nlm.nih.gov/compound/22901904>, 7 pages.
Pubchem, (2011). "N-(3,4-Dimethylphenyl)-2-(3-(4-fluorophenyl)-7-oxoisothiazolo[4,5-d]pyrimidin-6(7H)-yl]acetamide: CID 53124354," Available online at <https://pubchem.ncbi.nlm.nih.gov/compound/53124354)>, 7 pages.
Pubchem, (2011). "N,3-Dimethyl-N-[(pyridin-2-yl)methyl]-5-sulfamoylthiophene-2-carboxamide: CID 51106824," Available online at <https://pubchem.ncbi.nlm.nih.gov/compound/51106824>, 7 pages.
Pubchem, (2013). "MCULE-4868029218: SID 165919505," Available online at <https://pubchem.ncbi.nlm.nih.gov/substance/165919505>, 5 pages.
Pubchem, (2015). "ZINC35845049: SID 260692697," Available online at <https://pubchem.ncbi.nlm.nih.gov/substance/260692697>, 4 pages.
Pubchem, (2016). "Substance Record: SID 299402484," Available online at <https://pubchem.ncbi.nlm.nih.gov/substance/299402484>, 4 pages.
Pubchem, (2019). "N-(13-(Dimethylamino)phenyl]methyl]-N-methyl-5-methylsulfonylthiophene-2-carboxamide: CID 136548438," Available online at <https://pubchem.ncbi.nlm.nih.gov/compound/136548438>, 6 pages.
Pubchem, (2019). "N-Methyl-N-[(3-methylphenyl)methyl]-5-methylsulfonylthiophene-2-carboxamide: CID 136548429," Available online at <https://pubchem.ncbi.nlm.nih.gov/compound/136548429>, 7 pages.
Rizzo et al., (2016). "Characterization of two de novoKCNT1 mutations in children with malignant migrating partial seizures in infancy," Mol Cell Neurosci., 72:54-63.
Wilen et al., (1977). "Strategies in optical resolutions," Tetrahedron, 33:2725-2736.
Zhang et al., (2017). "Gene mutation analysis of 175 Chinese patients with early-onset epileptic encephalopathy," Clin Genet., 91(5):717-724.
Zhou et al., (2018). "Novel mutations and phenotypes of epilepsy-associated genes in epileptic encephalopathies," Genes Brain Behav., 17:e12456, 11 pages.

KCNT1 INHIBITORS AND METHODS OF USE

CROSS-REFERENCE TO RELATED APPLICATIONS

This application claims priority to U.S. Provisional Patent Application No. 63/108,588, filed Nov. 2, 2021, which is incorporated herein by reference in its entirety.

BACKGROUND

KCNT1 encodes sodium-activated potassium channels known as Slack (Sequence like a calcium-activated K⁺ channel). These channels are found in neurons throughout the brain and can mediate a sodium-activated potassium current $I_{KNa}$. This delayed outward current can regulate neuronal excitability and the rate of adaption in response to maintained stimulation. Abnormal Slack activity have been associated with development of early onset epilepsies and intellectual impairment. Accordingly, pharmaceutical compounds that selectively regulate sodium-activated potassium channels, e.g., abnormal KCNT1, abnormal $I_{KNa}$, are useful in treating a neurological disease or disorder or a disease or condition related to excessive neuronal excitability and/or KCNT1 gain-of-function mutations.

BRIEF SUMMARY

Described herein are compounds and compositions useful for preventing and/or treating a disease, disorder, or condition, e.g., a neurological disease or disorder, a disease, disorder, or condition associated with excessive neuronal excitability and/or a gain-of-function mutation in a gene, for example, KCNT1.

In one aspect, the present disclosure features a compound selected from the group consisting of:

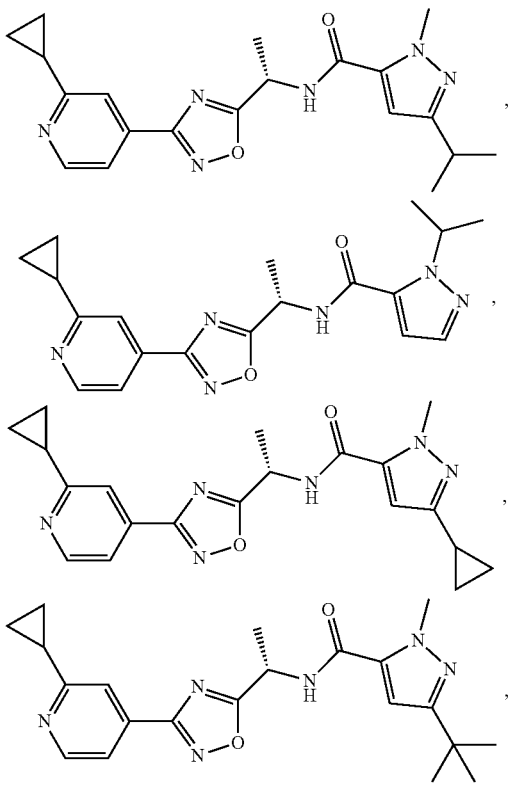

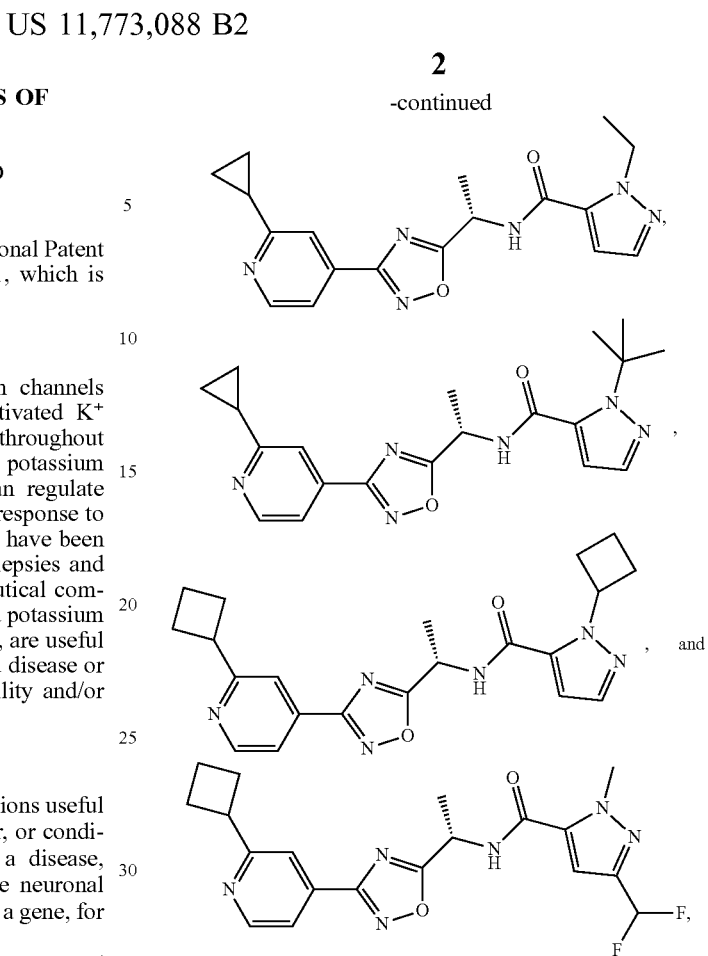

or a pharmaceutically acceptable salt thereof.

In another aspect, the present disclosure provides a pharmaceutical composition comprising a compound disclosed herein, or a pharmaceutically acceptable salt thereof, and a pharmaceutically acceptable excipient.

In another aspect, the present disclosure provides a method of treating a neurological disease or disorder, wherein the method comprises administering to a subject in need thereof a compound disclosed herein or a pharmaceutical composition disclosed herein (e.g., a pharmaceutical composition comprising a compound disclosed herein, or a pharmaceutically acceptable salt thereof, and a pharmaceutically acceptable excipient).

In another aspect, the present disclosure provides a method of treating a disease or condition associated with excessive neuronal excitability, wherein the method comprises administering to a subject in need thereof a compound disclosed herein or a pharmaceutical composition disclosed herein (e.g., a pharmaceutical composition comprising a compound disclosed herein, or a pharmaceutically acceptable salt thereof, and a pharmaceutically acceptable excipient).

In another aspect, the present disclosure provides a method of treating a disease or condition associated with a gain-of-function mutation of a gene (e.g., KCNT1), wherein the method comprises administering to a subject in need thereof a compound disclosed herein, or a pharmaceutical composition disclosed herein (e.g., a pharmaceutical composition comprising a compound disclosed herein, or a pharmaceutically acceptable salt thereof, and a pharmaceutically acceptable excipient).

In some embodiments, the neurological disease or disorder, the disease or condition associated with excessive neuronal excitability, or the disease or condition associated with a gain-of-function mutation of a gene (e.g., KCNT1) is epilepsy, an epilepsy syndrome, or an encephalopathy.

In some embodiments, the neurological disease or disorder, the disease or condition associated with excessive neuronal excitability, or the disease or condition associated with a gain-of-function mutation of a gene (e.g., KCNT1) is a genetic or pediatric epilepsy or a genetic or pediatric epilepsy syndrome.

In some embodiments, the neurological disease or disorder, the disease or condition associated with excessive neuronal excitability, or the disease or condition associated with a gain-of-function mutation of a gene (e.g., KCNT1) is a cardiac dysfunction.

In some embodiments, the neurological disease or disorder, the disease or condition associated with excessive neuronal excitability, or the disease or condition associated with a gain-of-function mutation of a gene (e.g., KCNT1) is selected from epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, Lennox Gastaut syndrome, seizures (e.g., Generalized tonic clonic seizures, Asymmetric Tonic Seizures), leukodystrophy, leukoencephalopathy, intellectual disability, Multifocal Epilepsy, Drug resistant epilepsy, Temporal lobe epilepsy, cerebellar ataxia).

In some embodiments, the neurological disease or disorder, the disease or condition associated with excessive neuronal excitability, or the disease or condition associated with a gain-of-function mutation of a gene (e.g., KCNT1) is selected from the group consisting of cardiac arrhythmia, sudden unexpected death in epilepsy, Brugada syndrome, and myocardial infarction.

In some embodiments, the neurological disease or disorder, the disease or condition associated with excessive neuronal excitability, or the disease or condition associated with a gain-of-function mutation of a gene (e.g., KCNT1) is selected from pain and related conditions (e.g. neuropathic pain, acute/chronic pain, migraine, etc).

In some embodiments, the neurological disease or disorder, the disease or condition associated with excessive neuronal excitability, or the disease or condition associated with a gain-of-function mutation of a gene (e.g., KCNT1) is a muscle disorder (e.g. myotonia, neuromyotonia, cramp muscle spasms, spasticity).

In some embodiments, the neurological disease or disorder, the disease or condition associated with excessive neuronal excitability, or the disease or condition associated with a gain-of-function mutation of a gene (e.g., KCNT1) is selected from itch and pruritis, ataxia and cerebellar ataxias.

In some embodiments, the neurological disease or disorder, the disease or condition associated with excessive neuronal excitability, or the disease or condition associated with a gain-of-function mutation of a gene (e.g., KCNT1) is selected from psychiatric disorders (e.g. major depression, anxiety, bipolar disorder, schizophrenia).

In some embodiments, the neurological disease or disorder or the disease or condition associated with excessive neuronal excitability and/or a gain-of-function mutation in a gene (e.g., KCNT1) is selected from the group consisting of learning disorders, Fragile X, neuronal plasticity, and autism spectrum disorders.

In some embodiments, the neurological disease or disorder, the disease or condition associated with excessive neuronal excitability, or the disease or condition associated with a gain-of-function mutation of a gene (e.g., KCNT1) is selected from the group consisting of epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

Other objects and advantages will become apparent to those skilled in the art from a consideration of the ensuing Detailed Description, Examples, and Claims.

DETAILED DESCRIPTION

As generally described herein, the present invention provides compounds and compositions useful for preventing and/or treating a disease, disorder, or condition described herein, e.g., a disease, disorder, or condition associated with excessive neuronal excitability, and/or a disease, disorder, or condition associated with gain-of-function mutations in KCNT1. Exemplary diseases, disorders, or conditions include epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, and Lennox Gastaut syndrome, seizures, leukodystrophy, leukoencephalopathy, intellectual disability, Multifocal Epilepsy, Generalized tonic clonic seizures, Drug resistant epilepsy, Temporal lobe epilepsy, cerebellar ataxia, Asymmetric Tonic Seizures) and cardiac dysfunctions (e.g., cardiac arrhythmia, Brugada syndrome, sudden unexpected death in epilepsy, myocardial infarction), pain and related conditions (e.g. neuropathic pain, acute/chronic pain, migraine, etc), muscle disorders (e.g. myotonia, neuromyotonia, cramp muscle spasms, spasticity), itch and pruritis, ataxia and cerebellar ataxias, psychiatric disorders (e.g. major depression, anxiety, bipolar disorder, schizophrenia), learning disorders, Fragile X, neuronal plasticity, and autism spectrum disorders.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

These and other exemplary substituents are described in more detail in the Detailed Description, Examples, and Claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19, and Gould, Salt selection for basic drugs, International Journal of Pharmaceutics, 33 (1986) 201-217. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (also "therapeutic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

In an alternate embodiment, the present invention contemplates administration of the compounds of the present invention or a pharmaceutically acceptable salt or a pharmaceutically acceptable composition thereof, as a prophylactic before a subject begins to suffer from the specified disease, disorder or condition. As used herein, "prophylactic treatment" contemplates an action that occurs before a subject begins to suffer from the specified disease, disorder or condition. As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein, a "disease or condition associated with a gain-of-function mutation in KCNT1" refers to a disease or condition that is associated with, is partially or completely caused by, or has one or more symptoms that are partially or completely caused by, a mutation in KCNT1 that results in a gain-of-function phenotype, i.e. an increase in activity of the potassium channel encoded by KCNT1 resulting in an increase in whole cell current.

As used herein, a "gain-of-function mutation" is a mutation in KCNT1 that results in an increase in activity of the potassium channel encoded by KCNT1. Activity can be assessed by, for example, ion flux assay or electrophysiology (e.g. using the whole cell patch clamp technique). Typically, a gain-of-function mutation results in an increase of at least or about 20%, 30%, 40%, 50%, 60%, 70%, 80%, 90%, 100%, 125%, 150%, 175%, 200%, 225%, 250%, 275%, 300%, 325%, 350%, 375%, 400% or more compared to the activity of a potassium channel encoded by a wild-type KCNT1.

Compounds and Compositions

In one aspect, the present disclosure provides a compound selected from the group consisting of:

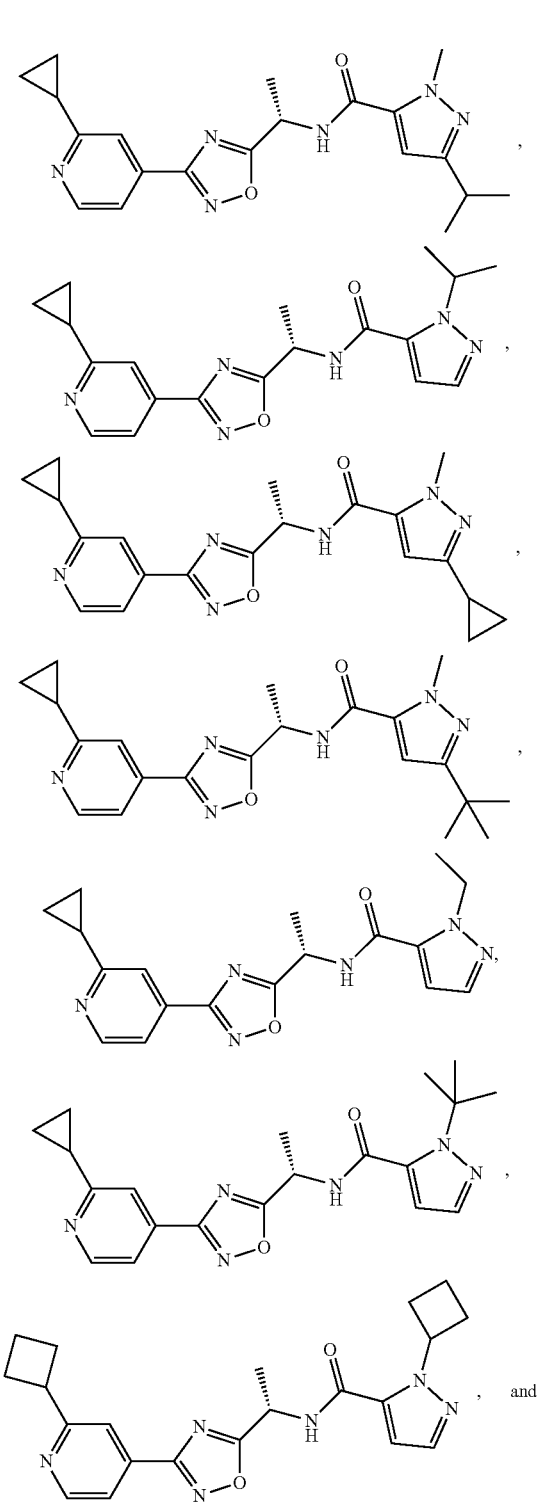

-continued

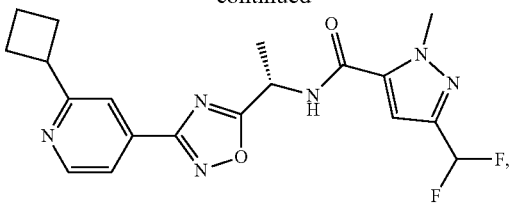

or a pharmaceutically acceptable salt thereof.

In typical embodiments, the present invention is intended to encompass the compounds disclosed herein, and the pharmaceutically acceptable salts, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, all polymorphs including polymorphs of hydrates and solvates, an enantiomer, a mixture of enantiomers, a diastereomer, a mixture of diastereomers, a stereoisomer or mixture of stereoisomers (pure or as a racemic or non-racemic mixture) of a compound described herein.

Methods of Treatment

The compounds and compositions described above and herein can be used to treat a neurological disease or disorder or a disease or condition associated with excessive neuronal excitability and/or a gain-of-function mutation in a gene (e.g., KCNT1). Exemplary diseases, disorders, or conditions include epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, developmental and epileptic encephalopathy (DEE), early infantile epileptic encephalopathy (EIEE), generalized epilepsy, focal epilepsy, multifocal epilepsy, temporal lobe epilepsy, Ohtahara syndrome, early myoclonic encephalopathy and Lennox Gastaut syndrome, drug resistant epilepsy, seizures (e.g., frontal lobe seizures, generalized tonic clonic seizures, asymmetric tonic seizures, focal seizures), leukodystrophy, hypomyelinating leukodystrophy, leukoencephalopathy, and sudden unexpected death in epilepsy, cardiac dysfunctions (e.g., cardiac arrhythmia, Brugada syndrome, myocardial infarction), pulmonary vasculopathy/hemorrhage, pain and related conditions (e.g. neuropathic pain, acute/chronic pain, migraine, etc), muscle disorders (e.g. myotonia, neuromyotonia, cramp muscle spasms, spasticity), itch and pruritis, movement disorders (e.g., ataxia and cerebellar ataxias), psychiatric disorders (e.g. major depression, anxiety, bipolar disorder, schizophrenia, attention-deficit hyperactivity disorder), neurodevelopmental disorder, learning disorders, intellectual disability, Fragile X, neuronal plasticity, and autism spectrum disorders.

In some embodiments, the neurological disease or disorder or the disease or condition associated with excessive neuronal excitability and/or a gain-of-function mutation in a gene (e.g., KCNT1) is selected from EIMFS, ADNFLE and West syndrome. In some embodiments, the neurological disease or disorder or the disease or condition associated with excessive neuronal excitability and/or a gain-of-function mutation in a gene (e.g., KCNT1) is selected from infantile spasms, epileptic encephalopathy, focal epilepsy, Ohtahara syndrome, developmental and epileptic encephalopathy and Lennox Gastaut syndrome. In some embodiments, the neurological disease or disorder or the disease or condition associated with excessive neuronal excitability and/or a gain-of-function mutation in a gene (e.g., KCNT1) is seizure. In some embodiments, the neurological disease or disorder or the disease or condition associated with excessive neuronal excitability and/or a gain-of-function mutation in a gene (e.g., KCNT1) is selected from cardiac arrhythmia, Brugada syndrome, and myocardial infarction.

In some embodiments, the neurological disease or disorder or the disease or condition associated with excessive neuronal excitability and/or a gain-of-function mutation in a gene (e.g., KCNT1) is selected from the group consisting of the learning disorders, Fragile X, intellectual function, neuronal plasticity, psychiatric disorders, and autism spectrum disorders.

Accordingly, the compounds and compositions thereof can be administered to a subject with a neurological disease or disorder or a disease or condition associated with excessive neuronal excitability and/or a gain-of-function mutation in a gene such as KCNT1 (e.g., EIMFS, ADNFLE, West syndrome, infantile spasms, epileptic encephalopathy, focal epilepsy, Ohtahara syndrome, developmental and epileptic encephalopathy, and Lennox Gastaut syndrome, seizures, cardiac arrhythmia, Brugada syndrome, and myocardial infarction).

EIMFS is a rare and debilitating genetic condition characterized by an early onset (before 6 months of age) of almost continuous heterogeneous focal seizures, where seizures appear to migrate from one brain region and hemisphere to another. Patients with EIMFS are generally intellectually impaired, non-verbal and non-ambulatory. While several genes have been implicated to date, the gene that is most commonly associated with EIMFS is KCNT1. Several de novo mutations in KCNT1 have been identified in patients with EIMFS, including V271F, G288S, R428Q, R474Q, R474H, R474C, I760M, A934T, P924L, G243S, H257D, A259D, R262Q, Q270E, L274I, F346L, C377S, R398Q, P409S, A477T, F502V, M516V, Q550del, K629E, K629N, I760F, E893K, M896K, R933G, R950Q, K1154Q (Barcia et al. (2012) Nat Genet. 44: 1255-1260; Ishii et al. (2013) Gene 531:467-471; McTague et al. (2013) Brain. 136: 1578-1591; Epi4K Consortium & Epilepsy Phenome/Genome Project. (2013) Nature 501:217-221; Lim et al. (2016) Neurogenetics; Ohba et al. (2015) Epilepsia 56:e121-e128; Zhou et al. (2018) Genes Brain Behav. e12456; Moller et al. (2015) Epilepsia. e114-20; Numis et al. (2018) Epilepsia. 1889-1898; Madaan et al. Brain Dev. 40(3):229-232; McTague et al. (2018) Neurology. 90(1):e55-e66; Kawasaki et al. (2017) J Pediatr. 191:270-274; Kim et al. (2014) Cell Rep. 9(5):1661-1672; Ohba et al. (2015) Epilepsia. 56(9): e121-8; Rizzo et al. (2016) Mol Cell Neurosci. 72:54-63; Zhang et al. (2017) Clin Genet. 91(5):717-724; Mikati et al. (2015) Ann Neurol. 78(6):995-9; Baumer et al. (2017) Neurology. 89(21):2212; Dilena et al. (2018) Neurotherapeutics. 15(4):1112-1126). These mutations are gain-of-function, missense mutations that are dominant (i.e. present on only one allele) and result in change in function of the encoded potassium channel that causes a marked increase in whole cell current when tested in Xenopus oocyte or mammalian expression systems (see e.g. Milligan et al. (2015) Ann Neurol. 75(4): 581-590; Barcia et al. (2012) Nat Genet. 44(11): 1255-1259; and Mikati et al. (2015) Ann Neurol. 78(6): 995-999).

ADNFLE has a later onset than EIMFS, generally in mid-childhood, and is generally a less severe condition. It is characterized by nocturnal frontal lobe seizures and can result in psychiatric, behavioural and cognitive disabilities in patients with the condition. While ADNFLE is associated with genes encoding several neuronal nicotinic acetylcholine receptor subunits, mutations in the KCNT1 gene have been implicated in more severe cases of the disease (Heron et al. (2012) Nat Genet. 44: 1188-1190). Functional studies of the mutated KCNT1 genes associated with ADNFLE indicated that the underlying mutations (M896I, R398Q, Y796H and R928C) were dominant, gain-of-function mutations (Milligan et al. (2015) Ann Neurol. 75(4): 581-590; Mikati et al. (2015) Ann Neurol. 78(6): 995-999).

West syndrome is a severe form of epilepsy composed of a triad of infantile spasms, an interictal electroencephalogram (EEG) pattern termed hypsarrhythmia, and mental retardation, although a diagnosis can be made one of these elements is missing. Mutations in KCNT1, including G652V and R474H, have been associated with West syndrome (Fukuoka et al. (2017) Brain Dev 39:80-83 and Ohba et al. (2015) Epilepsia 56:e121-e128). Treatment targeting the KCNT1 channel suggests that these mutations are gain-of-function mutations (Fukuoka et al. (2017) Brain Dev 39:80-83).

In one aspect, the present invention features a method of treating treat a disease or condition associated with excessive neuronal excitability and/or a gain-of-function mutation in a gene such as KCNT1 (for example, epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy (DEE), and Lennox Gastaut syndrome, seizures, leukodystrophy, leukoencephalopathy, intellectual disability, Multifocal Epilepsy, Generalized tonic clonic seizures, Drug resistant epilepsy, Temporal lobe epilepsy, cerebellar ataxia, Asymmetric Tonic Seizures) and cardiac dysfunctions (e.g., cardiac arrhythmia, Brugada syndrome, sudden unexpected death in epilepsy, myocardial infarction), pain and related conditions (e.g. neuropathic pain, acute/chronic pain, migraine, etc), muscle disorders (e.g. myotonia, neuromyotonia, cramp muscle spasms, spasticity), itch and pruritus, ataxia and cerebellar ataxias, psychiatric disorders (e.g. major depression, anxiety, bipolar disorder, schizophrenia), learning disorders, Fragile X, neuronal plasticity, and autism spectrum disorders) comprising administering to a subject in need thereof a compound disclosed herein or a pharmaceutical composition disclosed herein (e.g., a pharmaceutical composition comprising a compound disclosed herein, or a pharmaceutically acceptable salt thereof, and a pharmaceutically acceptable excipient).

In some examples, the subject presenting with a disease or condition that may be associated with a gain-of-function mutation in KCNT1 is genotyped to confirm the presence of a known gain-of-function mutation in KCNT1 prior to administration of the compounds and compositions thereof. For example, whole exome sequencing can be performed on the subject. Gain-of-function mutations associated with EIMFS may include, but are not limited to, V271F, G288S, R428Q, R474Q, R474H, R474C, I760M, A934T, P924L, G243S, H257D, A259D, R262Q, Q270E, L274I, F346L, C377S, R398Q, P409S, A477T, F502V, M516V, Q550del, K629E, K629N, I760F, E893K, M896K, R933G, R950Q, and K1154Q. Gain-of-function mutations associated with ADNFLE may include, but are not limited to, M896I, R398Q, Y796H, R928C, and G288S. Gain-of-function mutations associated with West syndrome may include, but are not limited to, G652V and R474H. Gain-of-function mutations associated with temporal lobe epilepsy may include, but are not limited to, R133H and R565H. Gain-of-function mutations associated with Lennox-Gastaut may include, but are not limited to, R209C. Gain-of-function mutations associated with seizures may include, but are not limited to, A259D, G288S, R474C, R474H. Gain-of-function mutations associated with leukodystrophy may include, but are not limited to, G288S and Q906H. Gain-of-function mutations associated with Multifocal Epilepsy may include, but are not limited to, V340M. Gain-of-function mutations associated with EOE may include, but are not limited to, F346L and A934T. Gain-of-function mutations associated with Early-onset epileptic encephalopathies (EOEE) may include, but are not limited to, R428Q. Gain-of-function mutations associated with developmental and epileptic encephalopathies may include, but are not limited to, F346L, R474H, and A934T. Gain-of-function mutations associated with epileptic encephalopathies may include, but are not limited to, L437F, Y796H, P924L, R961H. Gain-of-function mutations associated with Early Infantile Epileptic Encephalopathy (EIEE) may include, but are not limited to, M896K. Gain-of-function mutations associated with drug resistant epilepsy and generalized tonic-clonic seizure may include, but are not limited to, F346L. Gain-of-function mutations associated with migrating partial seizures of infancy may include, but are not limited to, R428Q. Gain-of-function mutations associated with Leukoencephalopathy may include, but are not limited to, F932I. Gain-of-function mutations associated with NFLE may include, but are not limited to, A934T and R950Q. Gain-of-function mutations associated with Ohtahara syndrome may include, but are not limited to, A966T. Gain-of-function mutations associated with infantile spasms may include, but are not limited to, P924L. Gain-of-function mutations associated with Brugada Syndrome may include, but are not limited to, R1106Q. Gain-of-function mutations associated with Brugada Syndrome may include, but are not limited to, R474H.

In other examples, the subject is first genotyped to identify the presence of a mutation in KCNT1 and this mutation is then confirmed to be a gain-of-function mutation using standard in vitro assays, such as those described in Milligan et al. (2015) Ann Neurol. 75(4): 581-590. Typically, the presence of a gain-of-function mutation is confirmed when the expression of the mutated KCNT1 allele results an increase in whole cell current compared to the whole cell current resulting from expression of wild-type KCNT1 as assessed using whole-cell electrophysiology (such as described in Milligan et al. (2015) Ann Neurol. 75(4): 581-590; Barcia et al. (2012) Nat Genet. 44(11): 1255-1259; Mikati et al. (2015) Ann Neurol. 78(6): 995-999; or Rizzo et al. Mol Cell Neurosci. (2016) 72:54-63). This increase of whole cell current can be, for example, an increase of at least or about 50%, 100%, 150%, 200%, 250%, 300%, 350%, 400% or more. The subject can then be confirmed to have a disease or condition associated with a gain-of-function mutation in KCNT1.

In particular examples, the subject is confirmed as having a KCNT1 allele containing a gain-of-function mutation (e.g. V271F, G288S, R398Q, R428Q, R474Q, R474H, R474C, G652V, I760M, Y796H, M896I, P924L, R928C or A934T).

The compounds disclosed herein II-g), (II-h), (II-i), (II-j), (II-k) or a pharmaceutically acceptable salt thereof) or the pharmaceutical composition disclosed herein (e.g., a pharmaceutical composition comprising a compound disclosed herein, or a pharmaceutically acceptable salt thereof, and a pharmaceutically acceptable excipient) can also be used therapeutically for conditions associated with excessive neuronal excitability where the excessive neuronal excitability is not necessarily the result of a gain-of-function mutation in KCNT1. Even in instances where the disease is not the result of increased KCNT1 expression and/or activity, inhibition of KCNT1 expression and/or activity can nonetheless result in a reduction in neuronal excitability, thereby providing a therapeutic effect. Thus, the compounds disclosed herein or the pharmaceutical composition disclosed herein (e.g., a pharmaceutical composition comprising a compound disclosed herein, or a pharmaceutically acceptable salt thereof, and a pharmaceutically acceptable excipient) can be used to treat a subject with conditions associated with excessive neuronal excitability, for example, epilepsy and other encephalopathies (e.g., epilepsy of infancy with migrating focal seizures (EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, and Lennox Gastaut syndrome, seizures) or cardiac dysfunctions (e.g., cardiac arrhythmia, Brugada syndrome, myocardial infarction), regardless of whether or not the disease or disorder is associated with a gain-of-function mutation in KCNT1.

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprising a disclosed compound, or pharmaceutically acceptable salt thereof, and a pharmaceutically acceptable carrier.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

List of Abbreviations

TEA triethylamine
DCM dichloromethane
EtOH ethanol
ACN acetonitrile
MeCN acetonitrile
TFA trifluoroacetic acid
DCC N,N'-dicyclohexylcarbodiimide
EtOAc ethyl acetate
HATU hexafluorophosphate azabenzotriazole tetramethyl uranium
DEA diethanolamine
SFC supercritical fluid chemistry
DIPEA N,N-diisopropylethylamine
DMSO dimethylsulfoxide
LCMS liquid chromatography-mass spectrometry Example 1. Synthesis of Compounds 1-6

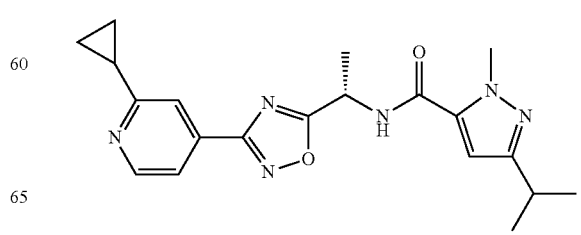

General Procedure for Compounds 1-6:

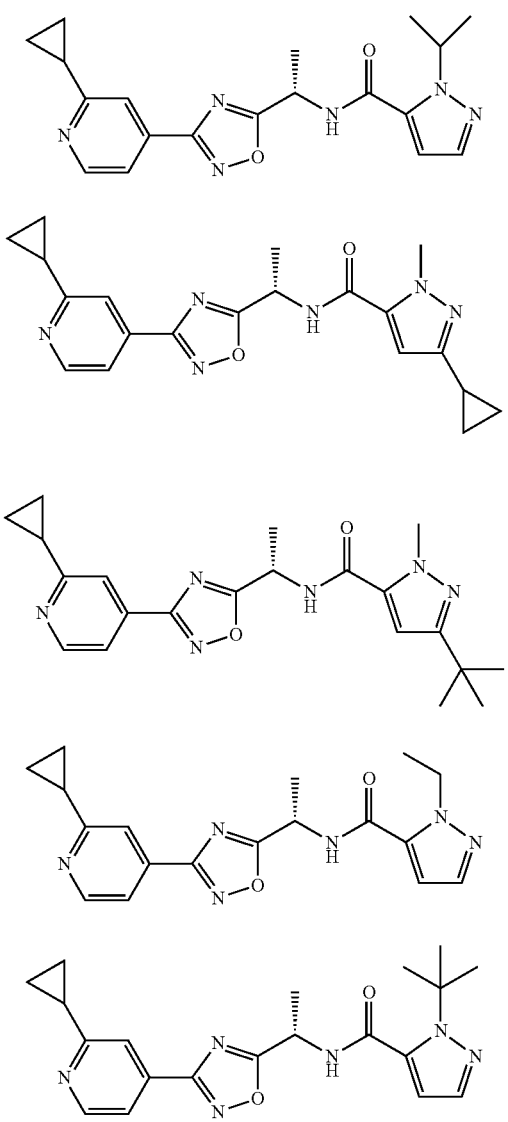

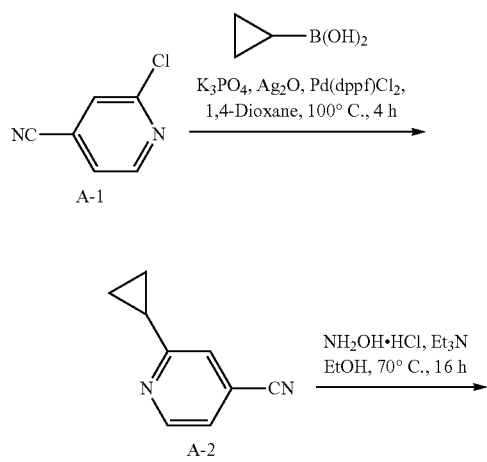

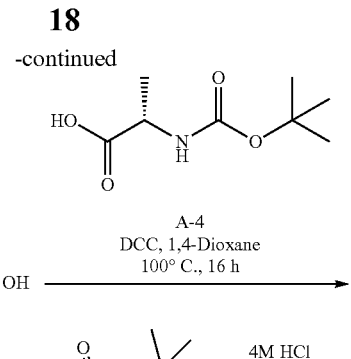

R = substituted pyrazole

Synthesis of 2-cyclopropylisonicotinonitrile (A-2)

To a stirred solution of A-1 (10.0 g, 72.18 mmol) in 1,4-dioxane (100 mL) was added K3PO4 (38.3 g, 180.44 mmol) and cyclopropylboronic acid (12.4 g, 144.35 mmol) at room temperature and purged with argon for 20 min. To the resulting solution was added silver oxide (3.35 g, 14.44 mmol) and Pd(dppf)Cl$_2$ (5.28 g, 7.22 mmol) at room temperature. The reaction mixture was further heated at 100° C. for 4 h. After completion of reaction, the reaction mixture was cooled to room temperature and filtered through pad of Celite and washed with ethyl acetate (100 mL). The filtrate collected was washed with water (3×100 mL). Organic layer was separated, dried over anhydrous Na$_2$SO$_4$, filtered and concentrated under reduced pressure resulting in the crude compound. The crude compound was purified by 100-200 mesh size silica gel column chromatography eluting with 5-10% of ethyl acetate in n-hexane to afford A-2 (5.50 g, 38.19 mmol, 53% yield) as a solid.

Synthesis of (Z)-2-cyclopropyl-N'-hydroxyisonicotinimidamide (A-3)

To a stirred solution of A-2 (5.50 g, 38.15 mmol) in ethanol (50 mL) was added triethyl amine (10.6 mL, 76.38 mmol) and hydroxylamine hydrochloride (4.00 g, 57.23 mmol) at room temperature. The reaction mixture was further heated at 70° C. for 16 h. After completion of the reaction, the reaction mixture was cooled to room temperature and concentrated under reduced pressure. The residue was diluted with water (50 mL) and extracted with DCM (3×50 mL). The organic layer was separated, dried over anhydrous $Na_2SO_4$, filtered and concentrated under reduced pressure to afford A-3 (6.00 g 33.86 mmol, 89% yield) as a solid which was used in the next step without further purification.

Synthesis of tert-butyl (S)-(1-(3-(2-cyclopropylpyridin-4-yl)-1,2,4-oxadiazol-5-yl)ethyl) carbamate (A-5)

To a stirred solution of A-3 (6.00 g, 33.86 mmol) in 1,4-Dioxane (60 mL) was added A-4 (7.05 g, 37.25 mmol) and DCC (7.67 g, 37.25 mmol) at room temperature. The reaction mixture was further heated at 100° C. for 16 h. The reaction mixture was cooled to room temperature and concentrated under reduced pressure. The residue was diluted with ethyl acetate (50 mL) and washed with water (2×20 mL). The organic layer was separated, washed with water (2×20 mL) followed by saturated brine solution (1×20 mL). The organic layer was separated, dried over anhydrous $MgSO_4$, filtered and concentrated under reduced pressure resulting in the crude compound. The crude compound was purified by 100-200 mesh size silica column chromatography eluting with 5-10% of ethyl acetate in n-hexane to afford A-5 (8.00 g, 24.25 mmol, 72% yield) as a liquid.

Synthesis of (S)-1-(3-(2-cyclopropylpyridin-4-yl)-1,2,4-oxadiazol-5-yl)ethan-1-amine (A-6)

To a stirred solution of A-5 (8.00 g, 24.21 mmol) in 1,4-Dioxane (20 mL) at 0° C. was added 4M HCl in dioxane (20 mL). The reaction mixture was allowed to attain room temperature and stirred for 6 h. The reaction mixture was concentrated under reduced pressure to dryness to afford A-6 HCl salt (6.00 g, 22.95 mmol, crude) as a solid which was used in the next step without further purification.

General Procedure for Amidation:

To a stirred solution of A-6 HCl salt (1 eq) and corresponding acid (1.2 eq/1.5 eq.) in DCM was added DIPEA (1.5 eq.) followed by HATU (1.5 eq.) at room temperature and stirred for 2 h. After completion of reaction, the reaction mixture was concentrated under reduced pressure and the crude residue was diluted with ethyl acetate. The organic layer was separated, washed with water followed by brine, dried over anhydrous $Na_2SO_4$, filtered and concentrated under reduced pressure to afford the crude compound. The crude compound was purified by flash column chromatography or Combiflash to afford the desired final compound.

Synthesis of (S)—N-(1-(3-(2-cyclopropylpyridin-4-yl)-1,2,4-oxadiazol-5-yl)ethyl)-3-isopropyl-1-methyl-1H-pyrazole-5-carboxamide (Compound 1)

Reaction was performed on 100 mg scale to afford 1 (0.049 g, 0.130 mmol, 22%). LCMS: 381.5 (M+H), Rt 1.904 min, Column: Kinetex EVO-C18 (3.0*50 mm, 2.6 μm); Mobile Phase: A: 0.025% Formic acid, B: Acetonitrile; T/B %: 0.01/5, 3/90, 5.5/5, 6/5; Flow rate: 0.8 mL/min (Gradient). HPLC: Rt 8.302 min; Column: X-Select CSH C18 (4.6×150) mm, 3.5 μm; Mobile phase: A: 0.1% Formic acid in water:ACN (95:05), B: ACN; Flow Rate: 1.0 mL/min. CHIRAL HPLC: Rt 6.904 min; Column: YMC CHIRAL ART CELLULOSE-SC, (250×4.6 mm, 5 u), Mobile Phase: A) n-Hexane+0.1% Iso-propyl amine, B) DCM:MeOH (50:50), Isocratic: 20% B; Wavelength: 292 nm, Flow: 1.0 mL/min. $^1$H NMR (400 MHz, DMSO-d6) δ 9.15 (d, 1H), 8.63 (d, 1H), 7.88 (s, 1H), 7.75-7.68 (m, 1H), 6.82 (s, 1H), 5.45-5.42 (m, 1H), 3.97 (s, 3H), 2.90-2.86 (m, 1H), 2.35-2.25 (m, 1H), 1.66 (d, 3H), 1.20 (d, 6H), 1.10-1.00 (m, 4H).

Synthesis of (S)—N-(1-(3-(2-cyclopropylpyridin-4-yl)-1,2,4-oxadiazol-5-yl)ethyl)-1-isopropyl-1H-pyrazole-5-carboxamide (Compound 2)

Reaction was performed on 100 mg scale to afford to afford 2 (62.32 mg, 0.17 mmol, 26%) as a solid. LCMS: 367.5 (M+H), Rt 1.868 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: Rt: 7.752 min; Column: X-Select CSH C18 (4.6×150) mm, 3.5 μm; Mobile phase: A: 0.1% Formic acid in water: ACN (95:05), B: ACN; Flow Rate: 1.0 mL/min. CHIRAL HPLC: Rt 6.474 min; Column: YMC CHIRAL ART CELLULOSE-SC, (250×4.6 mm, 5 u), Mobile Phase: A) n-Hexane+0.1% Iso-propyl amine, B) DCM:MeOH (50:50), Isocratic: 20% B; Wavelength: 292 nm, Flow: 1.0 mL/min. $^1$H NMR (400 MHz, DMSO-d6) δ 9.23 (d, 1H), 8.64 (d, 1H), 7.88 (s, 1H), 7.73 (d, 1H), 7.56-7.50 (m, 1H), 6.92-6.88 (m, 1H), 5.46-5.38 (m, 2H), 2.35-2.28 (m, 1H), 1.68 (d, 3H), 1.37-1.35 (m, 6H), 1.10-1.03 (m, 4H).

Synthesis of (S)-3-cyclopropyl-N-(1-(3-(2-cyclopropylpyridin-4-yl)-1,2,4-oxadiazol-5-yl)ethyl)-1-methyl-1H-pyrazole-5-carboxamide (Compound 3)

Reaction was performed on 100 mg scale to afford 3 (27.06 mg, 0.07 mmol, 12% yield) as a solid. LCMS: 379.2 (M+H), Rt 1.820 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: Rt: 7.670 min; Column: X-Select CSH C18 (4.6×150) mm, 3.5 μm; Mobile phase: A: 0.1% Formic acid in water: ACN (95:05), B: ACN; Flow Rate: 1.0 mL/min. CHIRAL HPLC: Rt 8.157 min; Column: YMC CHIRAL ART CELLULOSE-SC, (250×4.6 mm, 5 u), Mobile Phase: A) n-Hexane+0.1% Iso-propyl amine, B) DCM:MeOH (50:50), Isocratic: 20% B; Wavelength: 292 nm, Flow: 1.0 mL/min. $^1$H NMR (400 MHz, DMSO-d6) δ 9.23 (d, 1H), 8.64 (d, 1H), 7.88 (s, 1H), 7.73 (d, 1H), 7.54 (s, 1H), 6.91 (s, 1H), 5.46-5.38 (m, 2H), 2.35-2.28 (m, 1H), 1.68 (d, 3H), 1.37-1.35 (m, 6H), 1.10-1.03 (m, 4H).

Synthesis of (S)-3-(tert-butyl)-N-(1-(3-(2-cyclopropylpyridin-4-yl)-1,2,4-oxadiazol-5-yl)ethyl)-1-methyl-1H-pyrazole-5-carboxamide (Compound 4)

Reaction was performed on 100 mg scale to afford 4 (27.06 mg, 0.07 mmol, 12% yield) as a solid. LCMS: 395.6 (M+H), Rt 2.006 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: Rt: 8.617 min; Column: X-Select CSH C18 (4.6×150) mm, 3.5 μm; Mobile phase: A: 0.1% Formic acid in water: ACN (95:05), B: ACN; Flow Rate: 1.0 mL/min. CHIRAL HPLC: Rt 6.109 min; Column: YMC CHIRAL ART CELLULOSE-SC, (250×4.6 mm, 5 u), Mobile Phase: A) n-Hexane+0.1% Iso-propyl amine, B) DCM:MeOH (50:50), Isocratic: 20% B; Wavelength: 292 nm, Flow: 1.0 mL/min. ¹H NMR (400 MHz, DMSO-d6) δ 9.16-9.10 (m, 1H), 8.62-8.60 (m, 1H), 7.87 (s, 1H), 7.72-7.65 (m, 1H), 6.86 (s, 1H), 5.50-5.40 (m, 1H), 3.97 (s, 3H), 2.35-2.25 (m, 1H), 1.70-1.65 (m, 3H), 1.25 (s, 9H), 1.10-1.00 (m, 4H).

Synthesis of (S)—N-(1-(3-(2-cyclopropylpyridin-4-yl)-1,2,4-oxadiazol-5-yl)ethyl)-1-ethyl-1H-pyrazole-5-carboxamide (Compound 5)

Reaction was performed on 100 mg scale to afford 5 (20.55 mg, 0.060 mmol, 8%) as a solid. LCMS: 353.6 (M+H), Rt 1.743 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: Rt: 7.171 min; Column: X-Select CSH C18 (4.6×150) mm, 3.5 μm; Mobile phase: A: 0.1% Formic acid in water: ACN (95:05), B: ACN; Flow Rate: 1.0 mL/min. CHIRAL HPLC: Rt 7.650 min; Column: YMC CHIRAL ART CELLULOSE-SC, (250×4.6 mm, 5 u), Mobile Phase: A) n-Hexane+0.1% Iso-propyl amine, B) DCM:MeOH (50:50), Isocratic: 20% B; Wavelength: 292 nm, Flow: 1.0 mL/min. ¹H NMR (400 MHz, DMSO-d6) δ 9.30-9.20 (m, 1H), 8.68-8.62 (m, 1H), 7.90-7.87 (m, 1H), 7.80-7.75 (m, 1H), 7.52-7.48 (m, 1H), 6.96-6.94 (m, 1H), 5.50-5.40 (m, 1H), 4.48-4.45 (m, 2H), 2.38-2.28 (m, 1H), 1.75-1.65 (m, 3H), 1.32-1.25 (s, 3H), 1.09-1.04 (m, 4H).

Synthesis of (S)-1-(tert-butyl)-N-(1-(3-(2-cyclopropylpyridin-4-yl)-1,2,4-oxadiazol-5-yl)ethyl)-1H-pyrazole-5-carboxamide (Compound 6)

Reaction was performed on 150 mg scale to afford 6 (0.055 g, 0.144 mmol, 25% yield) as an oil. LCMS: 381.20 (M+H), $R_f$=2.534 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: $R_f$=7.277 min; Column: X-Select CSH C18 (150×4.6 mm, 3.5 μm). Mobile phase: A: 0.05% TFA: ACETONITRILE (95:05), B: ACETONITRILE: 0.05% TFA (95:05); Programme: T/B %: 0.01/10, 12/90, 16/90. Flow Rate: 1.0 mL/min; Diluent: Acetonitrile: Water. CHIRAL HPLC: $R_f$=10.08 min; Column: CHIRAL PAK IC (150×4.6 mm, 3 μm), Mobile Phase: A) 0.1% DEA in n-Hexane, B) EtOH:MeOH (1:1), A:B: 95:05; Flow: 0.7 mL/min. ¹H NMR (400 MHz, DMSO-d₆) δ ppm 9.42 (d, 1H), 8.61 (d, 1H), 7.83 (s, 1H), 7.64 (d, 1H), 7.42 (s, 1H), 6.58 (s, 1H), 5.40-5.37 (m, 1H), 2.39-2.21 (m, 1H), 1.65 (d, 3H), 1.58 (s, 9H), 0.97-1.01 (m, 4H).

Example 2: Synthesis of Compounds 7 and 8

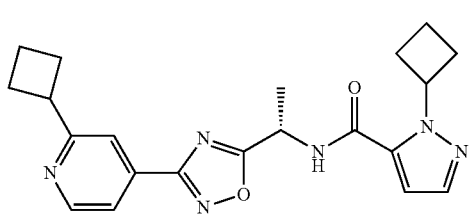

7

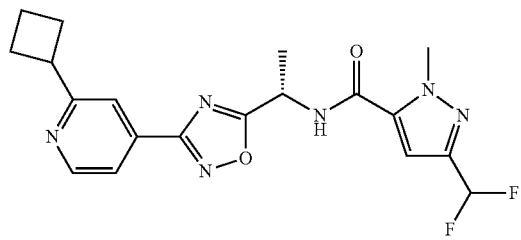

8

General Procedure for Compounds 7-8:

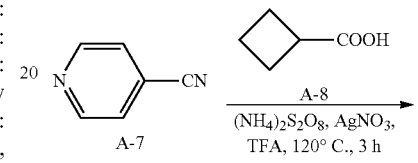

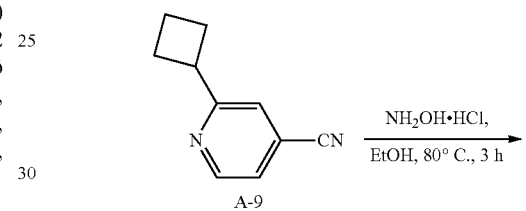

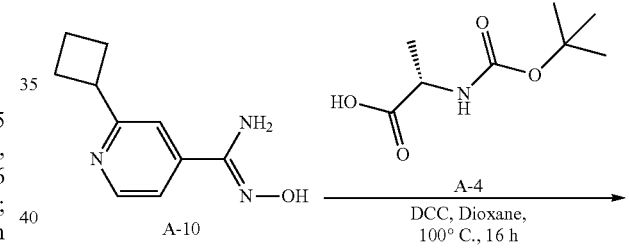

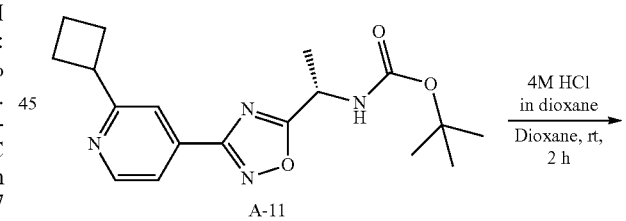

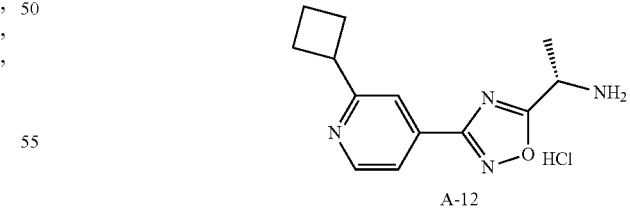

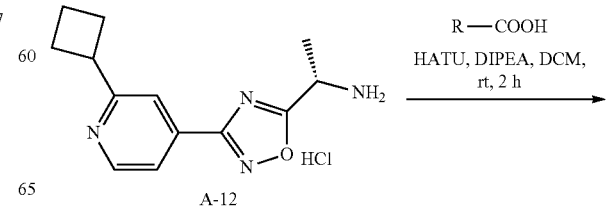

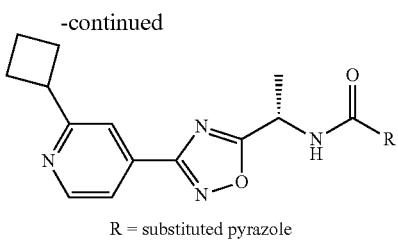

R = substituted pyrazole

Synthesis of 2-cyclobutylisonicotinonitrile (A-9)

To a stirred solution of A-7 (2.00 g, 19.21 mmol) in water (20 mL) and chlorobenzene (20 mL) was added A-8 (5.77 g, 57.63 mmol), ammonium persulfate (8.77 g, 38.42 mmol), TFA (1.41 mL, 18.37 mmol) and silver nitrate (0.326 g, 1.92 mmol). The reaction mixture was stirred at 120° C. for 3 h. The reaction mixture was diluted with water and extracted with ethyl acetate. The organic layer was dried over $Na_2SO_4$, filtered and evaporated to give the crude product which was purified by combiflash column chromatography using 8% Ethyl acetate in hexane as an eluent to give A-9 (2 g, 12.65 mmol, 67%) as an oil.

Synthesis of (Z)-2-cyclobutyl-N'-hydroxyisonicotinimidamide (A-10)

To a stirred solution of A-9 (2 g, 12.64 mmol) in EtOH (20 mL) was added hydroxylamine hydrochloride (1.32 g, 18.96 mmol) and TEA (2.55 g, 25.28 mmol) and stirred at 80° C. for 3 h. The reaction mixture was evaporated under reduced pressure. The residue was diluted with water and extracted with EtOAc. The organic layer dried over $Na_2SO_4$ filtered and evaporated to get crude product which was purified by silica gel column chromatography using 100-200 mesh silica and 8% Ethyl acetate/hexane as an eluent to give A-10 (2 g, 10.47 mmol, 83%) as an oil.

Synthesis of tert-butyl (S)-(1-(3-(2-cyclobutylpyridin-4-yl)-1,2,4-oxadiazol-5-yl)ethyl) carbamate (A-11)

To a stirred solution of A-10 (2 g, 10.46 mmol) in 1,4-Dioxane (20 mL) was added A-4 (2.18 g, 11.5 mmol) and DCC (2.37 g, 11.5 mmol). The reaction mixture was stirred at 100° C. for 16 h. The reaction mixture was diluted with water and extracted with ethyl acetate. The organic layer dried over $Na_2SO_4$ filtered and evaporated to give a crude product which was purified by combi flash column chromatography using 8% ethyl acetate in hexane as an eluent to give A-11 (3 g, 8.71 mmol, 83%) as an oil.

Synthesis of (S)-1-(3-(2-cyclobutylpyridin-4-yl)-1,2,4-oxadiazol-5-yl)ethan-1-amine Hydrochloride Salt (A-12)

To a stirred solution of A-11 (3 g, 8.71 mmol) in 1,4-Dioxane (10 mL) was added 4M HCl in 1,4-Dioxane (30 mL, 214.94 mmol) and stirred at RT for 2 h. The reaction mixture was concentrated under reduced pressure. The crude compound was triturated with diethyl ether to give compound A-12 HCl salt (2.5 g) as a solid.

General Procedure for Amidation:

To a stirred solution of A-12 HCl salt (1 eq) and the corresponding acid (1.2 eq/1.5 eq) in DCM was added DIPEA (1.5 eq.) followed by HATU (1.5 eq.) at room temperature and stirred for 2 h. After completion of the reaction, the mixture was concentrated under reduced pressure and the crude residue was diluted with ethyl acetate. The organic layer was separated, washed with water followed by brine, dried over anhydrous $Na_2SO_4$, filtered and concentrated under reduced pressure to afford the crude compound. The crude compound was purified by flash column chromatography or Combiflash to afford the desired final compound.

Synthesis of (S)-1-cyclobutyl-N-(1-(3-(2-cyclobutylpyridin-4-yl)-1,2,4-oxadiazol-5-yl)ethyl)-1H-pyrazole-5-carboxamide (Compound 7)

Reaction was performed on 50 mg scale to afford 7 (15 mg, 0.04 mmol, 21%) as a solid. LCMS: 393.55 (M+H), Rt 1.846 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: Rt 8.082 min; Column: X-Select CSH C18 (4.6×150) mm, 3.5 μm; Mobile phase: A: 0.1% Formic acid in water: ACN (95:05), B: ACN; Flow Rate: 1.0 mL/min. CHIRAL HPLC: Rt: 7.428 min; column: DIACEL CHIRALPAK-IG, (250×4.6 mm, 5 u), Mobile Phase: A) n-Hexane+0.1% Iso-propyl amine, B) DCM:MeOH (50:50), Isocratic: 30% B; Wavelength: 284 nm, Flow: 1.0 mL/min. $^1$H NMR (400 MHz, DMSO-d6) δ 8.93 (d, 1H), 8.73 (d, 1H), 7.94 (s, 1H), 7.75-7.72 (m, 2H), 6.68 (s, 1H), 5.45-5.43 (m, 1H), 4.93-4.89 (m, 1H), 3.81-3.76 (m, 1H), 2.45-2.35 (m, 3H), 2.32-2.28 (m, 5H), 2.06-2.01 (m, 1H), 1.82-1.80 (m, 3H), 1.70-1.66 (m, 3H).

Synthesis of (S)—N-(1-(3-(2-cyclobutylpyridin-4-yl)-1,2,4-oxadiazol-5-yl)ethyl)-3-(difluoromethyl)-1-methyl-1H-pyrazole-5-carboxamide (Compound 8)

Reaction was performed on 50 mg scale to afford 8 (15 mg, 0.04 mmol, 20%) as a solid. LCMS: 403.10 (M+H), Rt 1.807 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: Rt: 7.943 min %; Column: X-Select CSH C18 (4.6×150) mm, 3.5 μm; Mobile phase: A: 0.1% Formic acid in water: ACN (95:05), B: ACN; Flow Rate: 1.0 mL/min. CHIRAL HPLC: Rt: 7.650 min; column: YMC CHIRAL ART CELLULOSE-SC, (250×4.6 mm, 5 u), Mobile Phase: A) n-Hexane+0.1% Iso-propyl amine, B) DCM:MeOH (50:50), Isocratic: 20% B; Wavelength: 292 nm, Flow: 1.0 mL/min. $^1$H NMR (400 MHz, DMSO-d6) δ 8.93 (d, 1H), 8.76 (d, 1H), 7.86-7.78 (m, 2H), 7.26 (s, 1H), 7.05 (t, 1H), 5.48-5.45 (m, 1H), 4.08 (s, 3H), 2.33-2.29 (m, 4H), 2.08-2.02 (m, 1H), 1.88-1.85 (m, 1H), 1.68 (d, 3H), 1H merged in solvent peak.

Example 3: Efficacy of Exemplary Compounds in the Inhibition of KCNT1

KCNT1—Patch Clamp Assay

Inhibition of KCNT1 (KNa1.1, Slack) was evaluated using a tetracycline inducible cell line (HEK-TREX). Currents were recorded using the SyncroPatch 384PE automated, patch clamp system. Pulse generation and data collection were performed with PatchController384 V1.3.0 and DataController384 V1.2.1 (Nanion Technologies). The access resistance and apparent membrane capacitance were estimated using built-in protocols. Current were recorded in perforated patch mode (10 µM escin) from a population of cells. The cells were lifted, triturated, and resuspended at 800,000 cells/ml. The cells were allowed to recover in the cell hotel prior to experimentation. Currents were recorded at room temperature. The external solution contained the following (in mM): NaCl 105, NMDG 40, KCl 4, MgCl$_2$ 1, CaCl$_2$) 5 and HEPES 10 (pH=7.4, Osmolarity ~300 mOsm). The extracellular solution was used as the wash, reference and compound delivery solution. The internal solution contained the following (in mM): NaCl 70, KF 70, KCl 10, EGTA 5, HEPES 5 and Escin 0.01 (pH=7.2, Osmolarity ~295 mOsm). Escin is made at a 5 mM stock in water, aliquoted, and stored at −20° C. The compound plate was created at 2× concentrated in the extracellular solution. The compound was diluted to 1:2 when added to the recording well. The amount of DMSO in the extracellular solution was held constant at the level used for the highest tested concentration. A holding potential of −80 mV with a 100 ms step to 0 mV was used. Mean current was measured during the step to 0 mV. 100 µM Bepridil was used to completely inhibit KCNT1 current to allow for offline subtraction of non-KCNT1 current. The average mean current from 3 sweeps was calculated and the % inhibition of each compound was calculated. The % Inhibition as a function of the compound concentration was fit with a Hill equation to derive IC$_{50}$, slope, min and max parameters. If KCNT1 inhibition was less than 50% at the highest tested concentration or if an IC$_{50}$ could not be calculated, then a percent inhibition was reported in place of the IC$_{50}$.

Results from this assay are summarized in Table 1 below. In this table, "A" indicates IC$_{50}$ of less than or equal to 1 µM; "B" indicates inhibition of between 1 µM to 20 µM; and "C" indicates inhibition of greater than or equal to 20 µM.

TABLE 1

| Patent Compound No. | KCNT1-WT IC$_{50}$ (µM) |
|---|---|
| 1 | A |
| 2 | A |
| 3 | A |
| 4 | A |
| 5 | A |
| 6 | A |
| 7 | B |
| 8 | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A compound selected from the group consisting of:

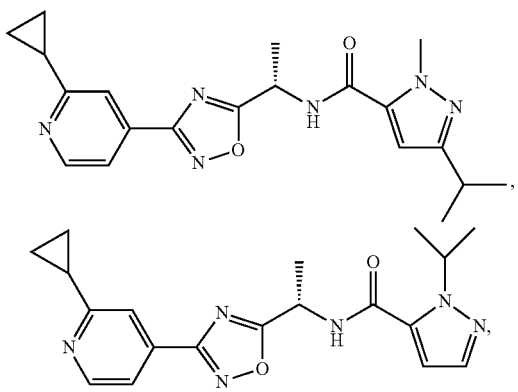

-continued

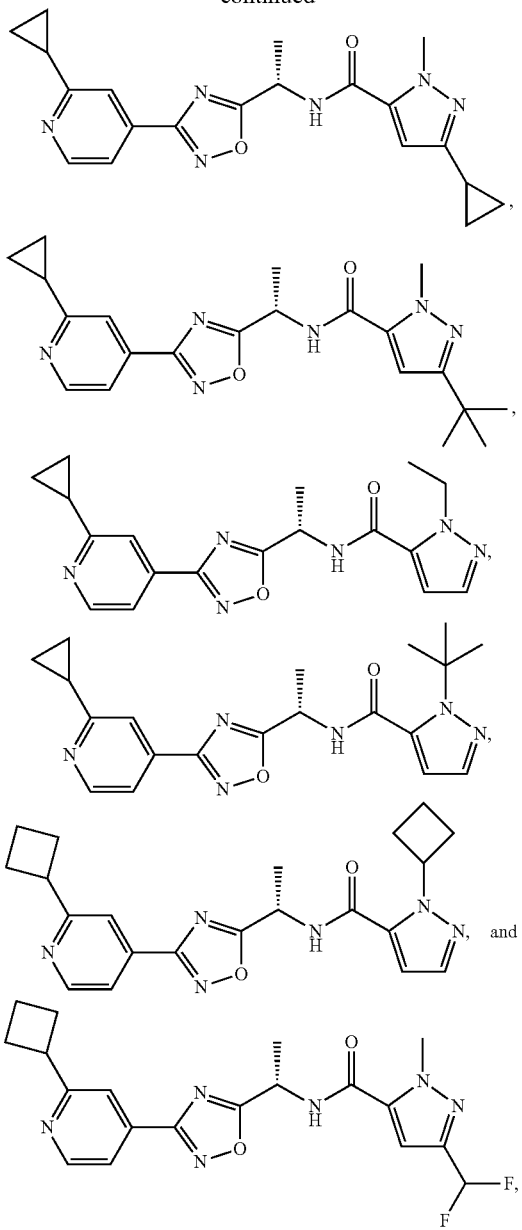

or a pharmaceutically acceptable salt thereof.

2. A pharmaceutical composition comprising:
a compound of claim 1, or a pharmaceutically acceptable salt thereof; and
a pharmaceutically acceptable excipient.

3. A method of treating a neurological disease or disorder, or a disease or condition associated with excessive neuronal excitability, or a disease or condition associated with a gain-of-function mutation of a gene, the method comprising:
administering to a subject in need thereof a compound of claim 1, or a pharmaceutically acceptable salt thereof.

4. The method of claim 3, wherein a pharmaceutical composition comprising the compound of claim 1, or a pharmaceutically acceptable salt thereof, and a pharmaceutically acceptable excipient, is administered to the subject.

5. The method of claim 3, wherein the neurological disease or disorder, the disease or condition associated with excessive neuronal excitability, or the disease or condition associated with a gain-of-function mutation of a gene is epilepsy, an epilepsy syndrome, or an encephalopathy.

6. The method of claim 3, wherein the neurological disease or disorder, the disease or condition associated with excessive neuronal excitability, or the disease or condition associated with a gain-of-function mutation of a gene is a genetic or pediatric epilepsy or a genetic or pediatric epilepsy syndrome.

7. The method of claim 3, wherein the neurological disease or disorder, the disease or condition associated with excessive neuronal excitability, or the disease or condition associated with a gain-of-function mutation of a gene is a cardiac dysfunction.

8. The method of claim 3, wherein the neurological disease or disorder, the disease or condition associated with excessive neuronal excitability, or the disease or condition associated with a gain-of-function mutation of a gene is:
epilepsy of infancy with migrating focal seizures (EIMFS);
malignant migrating focal seizures of infancy (MMFSI);
autosomal dominant nocturnal frontal lobe epilepsy (ADNFLE);
West syndrome;
infantile spasms;
epileptic encephalopathy;
focal epilepsy;
Ohtahara syndrome;
developmental and epileptic encephalopathy;
Lennox Gastaut syndrome;
seizures;
leukodystrophy;
leukoencephalopathy;
intellectual disability;
Multifocal Epilepsy;
Drug resistant epilepsy;
Temporal lobe epilepsy; or
cerebellar ataxia.

9. The method of claim 8, wherein the seizures are Generalized tonic clonic seizures, or Asymmetric Tonic Seizures.

10. The method of claim 3, wherein the neurological disease or disorder, the disease or condition associated with excessive neuronal excitability, or the disease or condition associated with a gain-of-function mutation of a gene is cardiac arrhythmia, sudden unexpected death in epilepsy, Brugada syndrome, or myocardial infarction.

11. The method of claim 3, wherein the neurological disease or disorder, the disease or condition associated with excessive neuronal excitability, or the disease or condition associated with a gain-of-function mutation of a gene is pain and related conditions.

12. The method of claim 11, wherein the pain and related conditions is neuropathic pain, acute pain, chronic pain, or migraine.

13. The method of claim 3, the neurological disease or disorder, the disease or condition associated with excessive neuronal excitability, or the disease or condition associated with a gain-of-function mutation of a gene is a muscle disorder.

14. The method of claim 13, wherein the muscle disorder is myotonia, neuromyotonia, cramp muscle spasms, or spasticity.

15. The method of claim 3, wherein the neurological disease or disorder, the disease or condition associated with excessive neuronal excitability, or the disease or condition associated with a gain-of-function mutation of a gene is itch and pruritis, ataxia or cerebellar ataxias.

16. The method of claim 3, wherein the neurological disease or disorder, the disease or condition associated with excessive neuronal excitability, or the disease or condition associated with a gain-of-function mutation of a gene is a psychiatric disorder.

17. The method of claim 16, wherein the psychiatric disorder is major depression, anxiety, bipolar disorder, or schizophrenia.

18. The method of claim 3, wherein the neurological disease or disorder or the disease or condition associated with excessive neuronal excitability and/or a gain-of-function mutation in a gene is a learning disorder, Fragile X, neuronal plasticity, or an autism spectrum disorder.

19. The method of claim 3, wherein the neurological disease or disorder, the disease or condition associated with excessive neuronal excitability, or the disease or condition associated with a gain-of-function mutation of a gene is:
  epileptic encephalopathy with SCN1A, SCN2A, and/or SCN8A mutations;
  early infantile epileptic encephalopathy;
  Dravet syndrome;
  Dravet syndrome with SCN1A mutation;
  generalized epilepsy with febrile seizures;
  intractable childhood epilepsy with generalized tonic-clonic seizures;
  infantile spasms;
  benign familial neonatal-infantile seizures;
  focal epilepsy with SCN3A mutation;
  cryptogenic pediatric partial epilepsy with SCN3A mutation;
  sudden unexpected death in epilepsy (SUDEP);
  Rasmussen encephalitis;
  malignant migrating partial seizures of infancy;
  autosomal dominant nocturnal frontal lobe epilepsy;
  KCNQ2 epileptic encephalopathy; or
  KCNT1 epileptic encephalopathy.

* * * * *